(12) United States Patent
Crosa Dorado

(10) Patent No.: US 6,350,250 B1
(45) Date of Patent: Feb. 26, 2002

(54) VACUUM DOSING DEVICE

(76) Inventor: Valentin Lorenzo Crosa Dorado, 26 de Marzo 1319 apartamento 3, Ciudadano Uruguayo (UY)

(*) Notice: Subject to any disclaimer, the term of this patent is extended or adjusted under 35 U.S.C. 154(b) by 0 days.

(21) Appl. No.: 09/366,495

(22) Filed: Aug. 3, 1999

(30) Foreign Application Priority Data

Aug. 12, 1998 (UY) .................................................. 25.136

(51) Int. Cl.[7] .............................................. A61M 1/00
(52) U.S. Cl. ...................................................... 604/35
(58) Field of Search .............................. 604/35, 30–36, 604/45, 27, 118, 119, 128, 129

(56) References Cited

U.S. PATENT DOCUMENTS

| | | | | |
|---|---|---|---|---|
| 3,469,582 A | * | 9/1969 | Jackson | 128/276 |
| 4,356,823 A | * | 11/1982 | Jackson | 128/276 |
| 6,117,134 A | * | 9/2000 | Cunningham et al. | 606/49 |
| 6,129,701 A | * | 10/2000 | Cimino | 604/35 |

OTHER PUBLICATIONS

Inventor's Statement with Translation—Describing prior art of unknown date assumed prior to filing date of application.

* cited by examiner

Primary Examiner—Anhtuan T. Nguyen
Assistant Examiner—Ann Y. Lam
(74) Attorney, Agent, or Firm—Welsh & Katz, Ltd.

(57) ABSTRACT

A device for dosing vaccum, mainly for medical applications, such as tracheal suction, consists of: (a) a tube with a cylindrical section with two troncoconical ends; said tube has small outlet holes and a middle partition wall; (b) a cylindrical rubber tube; (c) a cylindrical body or container which forms a clearance with the wall of said rubber tube; (d) a valve device with a lever which allows to open the vaccum circuit; (e) a stem projecting slightly over the surface of the lid of said valve.

In stand-by state the rubber tube closes the outlet holes and vaccum is excluded. Moving forward the stem communicates the inside of the body, expanding the rubber tube and allowing suction of air or intaken material.

It permits a close control of the vaccum, with a complete closure in stand-by and immediate start of suction on demand.

Possible contamination of operator, as well as the intake of strange materials is prevented. Its plastic and rubber construction facilitate disposable use to avoid cross contamination.

9 Claims, 5 Drawing Sheets

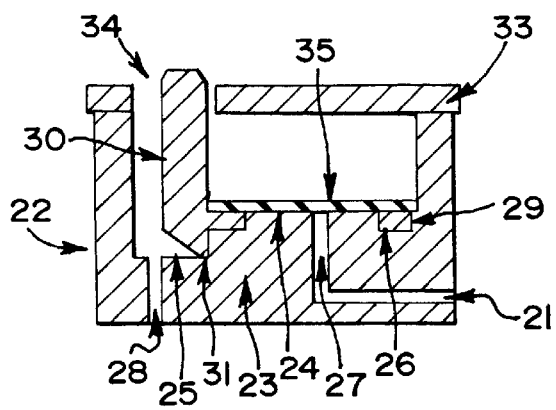
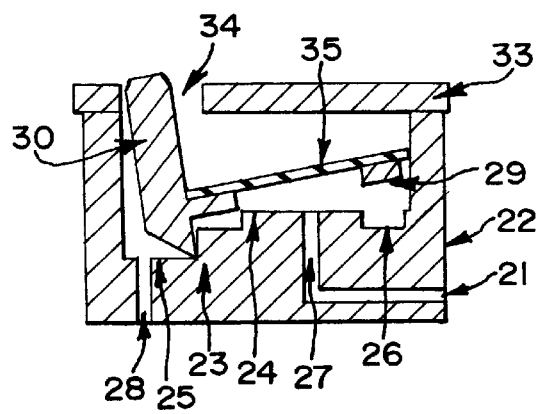
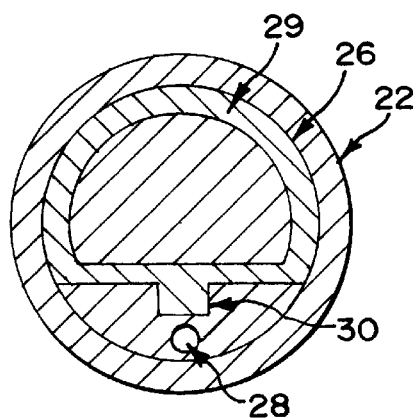
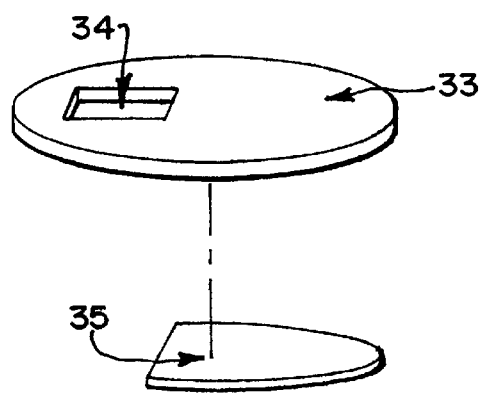
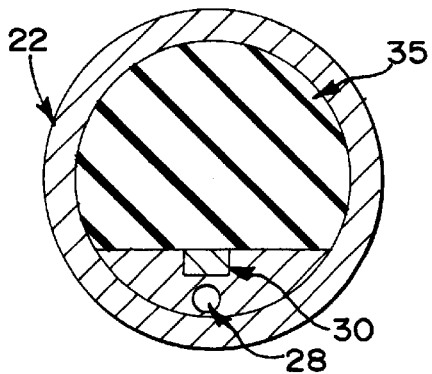
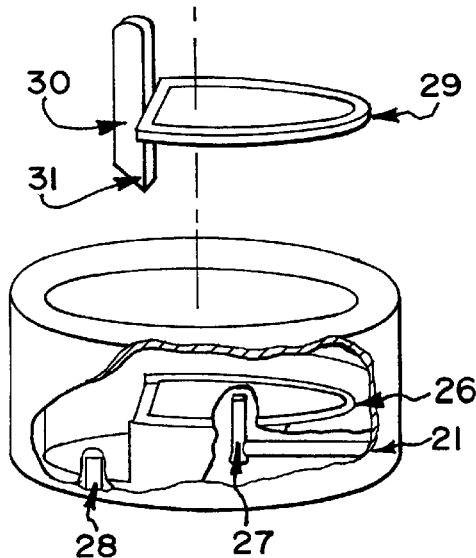

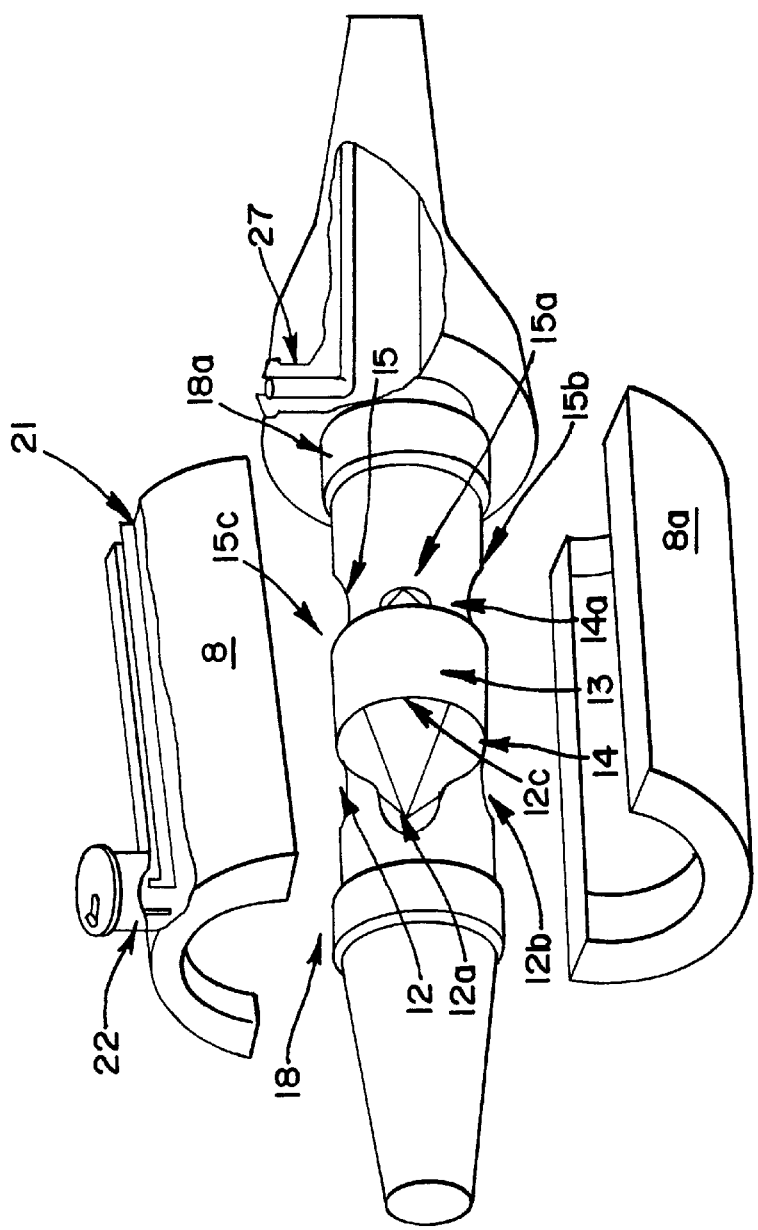
FIG.12
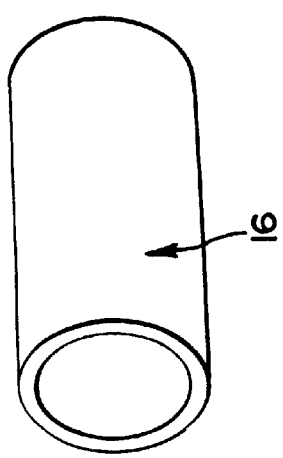

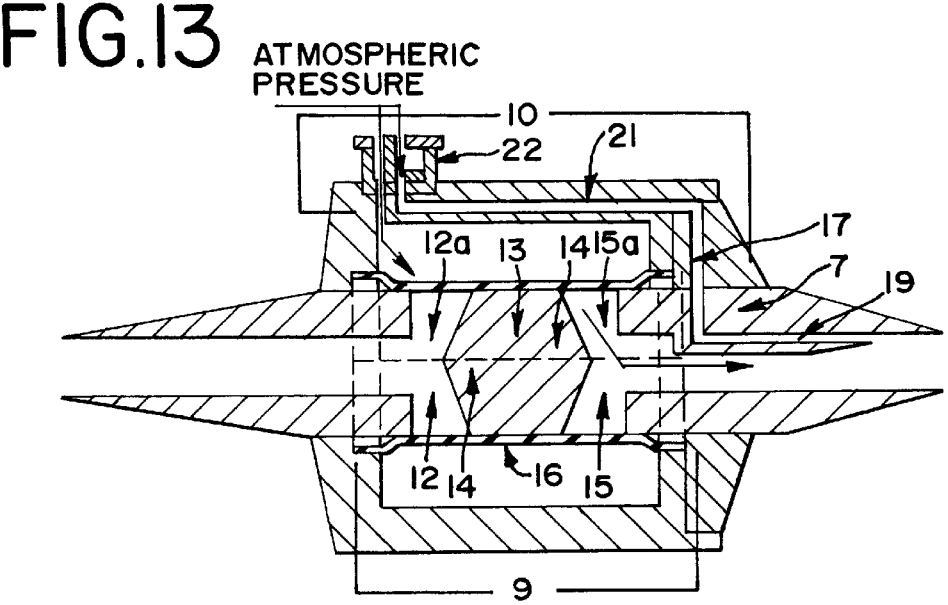
FIG.13 ATMOSPHERIC PRESSURE
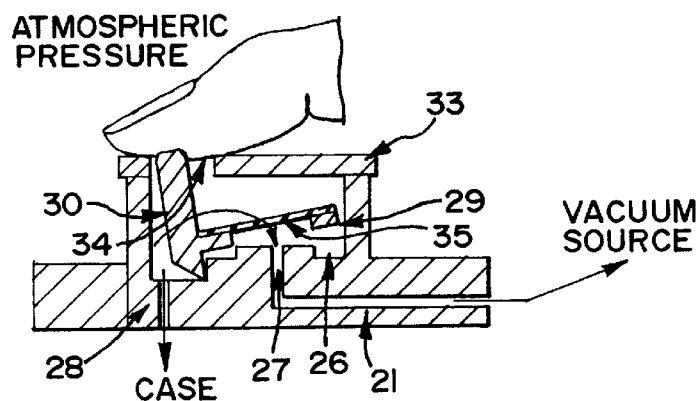
FIG.14 ATMOSPHERIC PRESSURE
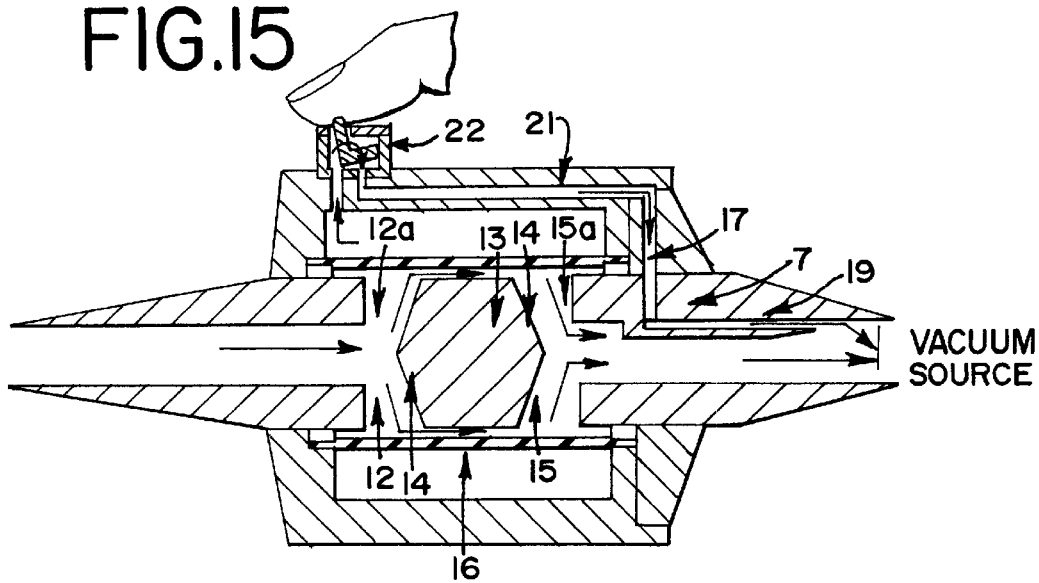
FIG.15

VACUUM DOSING DEVICE

TECHNICAL FIELD OF THE INVENTION

The invention relates to an application of mechanics to medicine. It deals with improvements in vacuum dosing devices used in surgical centers and other hospitalization areas including intensive care units of hospitals.

BACKGROUND OF THE INVENTION

The invention introduces a series of improvements in the operation of the instrument described in U.S. Pat. No. 13,437 (Ser. No. 23,472). Although the instrument disclosed in the above mentioned Patent has a vacuum saving function, it shows some imperfections in its operation as noted below.

(a) The closure produced by flattening the rubber tube is not perfect. As it collapses, said tube leaves in both corners (FIG. 1—1), a space along the tube, through which the vacuum unit continues drawing in ambient air during the stand-by state. Due to its flattened shape, the rubber tube frequently does not perfectly fit in the tube cylinder thus leaving a space (2) which continues with the space mentioned in (a), and through which air is permanently lost.

The hole (5) that communicates the ambient air with the inside of the case (3), through the hole (4) in the case, and the latter with the vacuum system, permits a vacuum loss which, though small, is permanent.

As the aspirated material passes in front of the hole (5), a certain amount of said material (6) enters the case (3) contaminating the finger that occludes its hole.

During the production process, both solid pieces need to be connected to a soft rubber tube, and subsequently the resulting set, which is also soft, must be inserted and fixed to the case holes; this assembly operation is therefore complicated and slow.

DESCRIPTION WITH REFERENCE TO DRAWINGS

The device comprises a solid tube (Sheet 2, FIGS. 5–7) which passes through a hollow case (8). The ends of said tube have a troncoconical shape. Said tube has two sections. one section (9) plays the role of keeping the system tightly occluded in the stand-by state. The other section (10) has a mechanism that controls the closing or opening of the occlusion section (9) described before, by regulating vacuum supply.

The occlusion section (9) starts at a troncoconical tube (11) which continues with a cylindrical tube (7) which has four holes (12, 12a, 12b and 12c) with a diameter of about 4 mm, located about 5 mm from its origin; said holes are in such a position that they are located in the same circular section as said tube and diametrically opposite to one another. Immediately after said holes, the tube clearance is interrupted by a partition wall (13), the free face of which projects into the tube in the form of a square base pyramid (14), the four sides of which face the four holes (12, 12a, 12b and 12c). Said partition wall (13) is about 15 mm thick. Immediately after the partition wall, the clearance of the tube is restored. At the level of the start of the clearance of said tube, there are four other holes (15, 15a, 15b and 15c) which are similar in diameter and position to holes (12, 12a, 12b and 12c) and have a similar relation with the other free face of the partition wall (14a) which has a similar square base pyramidal shape. The occlusion section is covered by an ellastic element, in this case a rubber tube (16) that has an internal diameter equal to the outside diameter of tube (7). At the beginning and at the end of the occlusion section, the tube (7) shows an increase (18 and 18a) in its outside diameter in the order of 0.5 mm on a length of 5 mm. Said enlargements coincide with both ends of the rubber tube (16). The occlusion section continues with the opening control section (10).

In the opening control section, the tube shows on its top face a perforation (17) which goes through the entire tube (7). The inner hole of the perforation (17) communicates with a semicircular section deflector gutter (19) which begins just before said hole and extends along the internal face of the tube (7), connecting the inside of said tube with the inside of the case (8). The opening and closing control section is continued by a troncoconical end (11a) similar to that of the occlusion section.

The case (8) is constituted by a cylindrical box longitudinally divided in two pieces which are assembled to each other (8 and 8a). When assembled, the heads determine a hole (20) with a diameter that is smaller than that of the set: the enlargements (18 and 18a) plus the thickness of the rubber tube wall (16), so that they act as fixing straps of the rubber tube (16).

A thin tube (21) goes through the thickness of the wall of the top half of the case (8a), and then goes down through the thickness of one of the heads and connects with the perforation (17) of the opening control section of the tube (7). The other end of the thin tube (21) communicates with a valve device consisting of a cylindrical box (22) (Sheet 3, FIGS. 6 to 11), which has a diameter of about 15 mm and a height of 10 mm and is located in the top half (8a) of the case. Said box is open to the outside. The bottom (23) of said box comprises two stepped planes of different sizes. The major plane (24) has an extension equivalent to tree quarters of the circular surface of said bottom and is the highest step with a difference of three millimeters from the minor plane (25). Along the entire contour of the major plane (24), there is a rectangular section gutter (26). In the center of said major plane (24) there appears a thin tube (27) which communicates with the tube (21) which goes longitudinally along the wall of the case, communicating the inside of the box (22) and the vacuum system, through the perforation (17).

In the center of the minor lower plane (24) of the bottom of said box, there is a perforation (28) that goes through the case wall and communicates the inside of said case with the ambient air. Inside the rectangular section gutter (26) there is a piece (29) with the same shape and section but with such a size that it is flush with the surface of the main step (24) and that it further permits an easy displacement of entry and outlet of the gutter (26) (FIG. 7). Said piece (29) is consolidate with a rod (30) located perpendicularly in the central part of the straight section of said piece (29). One of the ends (31) of said rod has a bevelled shape with the sharp edge resting on the dihedral angle formed by the minor plane (25) and the flat face (31) that joins both planes. The side of the rod facing the bevel contacts the face (31) of the bottom of the box (22). The end of the rod facing the bevelled end (31) is rounded. Said rod has such a length that it slightly projects over the outer surface of the lid (33) of said box. Said lid shows a rectangular shaped opening (34) wherein the rounded end of the rod is located. Said opening has such a size that it permits a free displacement of the rod only in the forward and backward direction and from the vertical position forwards, acting as a stop and a guide. A rubber sheet (35) shaped as said larger section of the bottom (24) but having a slightly smaller size so that its displacement is not obstructed, rests on the plane formed by the larger section of the bottom and the piece (29).

Operation

In the stand-by state (Sheet 5, FIG. 12), the system is completely occluded because the rubber tube is closely attached to the outlet holes (15, 15a, 15b and 15c) of the occlusion section by the suction action acting on the inner surface of the tube which presses it against the rigid tube wall (7), plus the atmospheric pressure acting in the same direction on its outer surface.

Similarly, the vacuum acting on the rubber sheet (35) through the tube (21) attaches it firmly to the inlet hole of said tube, preventing any communication with the vacuum system.

When the operator's finger presses the hole (34) of the valve (22) lid, it actuates the vacuum control section by a dual effect:

It cuts the communication of the inside of the case with the ambient air, and it displaces forward the projecting end of the lever (30) which, having the bevel (31) as rotation center, rises the piece (29) together with the rubber sheet (35). The operator's action results in the communication of the inside of the case, excluded from the atmosphere by the pressure the finger on the hole (34), with the vacuum source. This draws out the air contained in the case (FIG. 13). The resulting vacuum changes the conditions that characterized the stand-by state. The dual effect of the occlusion caused by the interaction of suction plus atmospheric pressure is altered and substituted by the vacuum inside the case that expands the rubber tube (16), which allows passage of air or aspirated material between the inlet holes of the occlusion section (12, 12a, 12b and 12c) and the outlet holes (15, 15a, 15b and 15c). The aspirated material passes by at the level of the hole (17) protected by the deflector (19), preventing the ingress into the case.

When the finger is released, the stand-by state is instantly restored, and the flow through the device is interrupted.

Advantages

The invention exhibits a series of advantages over the invention disclosed in U.S. Pat. No. 13,437 (Ser. No. 23,472).

It allows a close control of the use of vacuum. Occlusion in the stand-by state is perfect. Both start and stop of aspiration are immediately produced.

Aspiration is permanently and instantly available, making this device a very useful resource in treating patients who must be submitted to frequent tracheal aspiration maneuvers. Those maneuvers must frequently be made in emergency situations caused by a sudden obstruction of the intubation catheter, where the delay is a critical factor.

Its design allows the use of a high range of vacuum levels, tolerating the effects of the high negative pressures generated by the most powerful equipments used in hospitals. It can be used in the aspiration of septic material without risk of contamination for the operator. Manufacturing of its pieces (except for the ellastic pieces) in injected plastic material and its easy process of assembly allows to achieve a low cost disposable instrument.

Its disposable nature reduces the risks of cross contamination among patients which is observable when employing non-disposable materials.

Its effective occlusion in the stand-by state prevents the aspiration of harmful materials (yarn, cotton fibers, vandage pieces, etc.) that obstruct the filters of the vacuum unit, which require frequent maintenance, during which the machine remains inactive.

The systematic use of this instrument in every open outlet of the system prevents vacuum waste, increasing the duration of the unit, spacing out maintenance tasks and permitting that, when planning the installation of a vacuum source, units with a much lower power may be installed with the corresponding savings in the investment.

GENERAL EXPLANATION OF THE DRAWINGS

In order to contribute to understanding the description made above, sheets with the figures mentioned above and the reference numbers used are attached hereto.

Sheet 1. Example of the operation imperfections of the art disclosed in U.S. Pat. No. 13,437 (Ser. No. 23,472).

FIG. 1. A scheme of the reason of vacuum waste due to the bad fitting of the flattened rubber tube and the rigid cylindrical tube.

FIG. 2. A scheme showing the imperfect closure of the collapsed flattened rubber tube.

FIG. 3. A scheme showing the vacuum loss in the stand-by state through the hole.

FIG. 4. A scheme showing the possibility of contamination of the operator's finger during the operation of the cited art.

Sheet 2. Example of the art disclosed in this patent application.

FIG. 5. A sagittal section view of the art disclosed herein.

FIG. 6. A cross section view of the art presented at the level of a head of the case (section a-b).

Sheet 3. Example of the occlusion control valve.

FIG. 7. Sagittal section view of the occlusion control valve in its closed position, in the stand-by state.

FIG. 8. Sagittal section view of the occlusion control valve in its opened position.

FIG. 9. Cross section view of the occlusion control valve without the rubber sheet.

FIG. 10. Cross section view of the occlusion control valve with the rubber sheet.

FIG. 11. Exploded view of the occlusion control valve.

Sheet 4

FIG. 12. Exploded view of the art presented.

Sheet 5. Example of operation of the art presented.

FIG. 13 is a cross section view of the art presented in the stand-by state.

FIG. 14 is a cross section view of the occlusion control valve in operation.

FIG. 15 is a cross section view of the art presented in operation.

Figure 1:
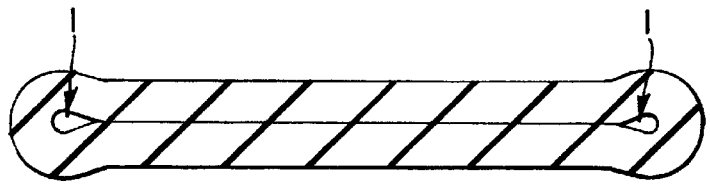
Figure 2:
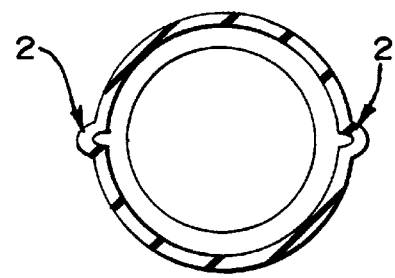
Figure 3:
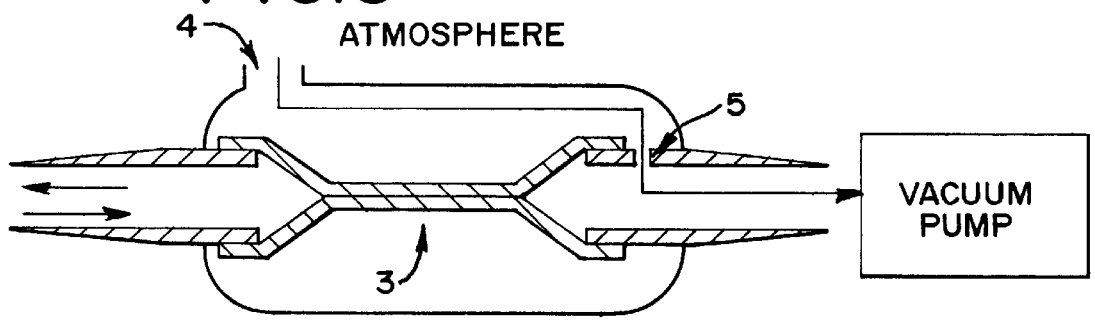
Figure 4:
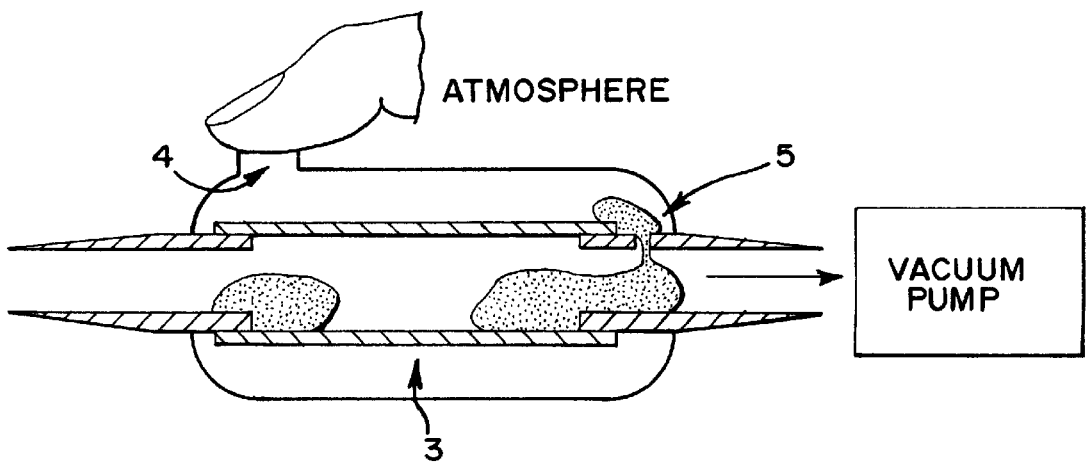
Figure 5:
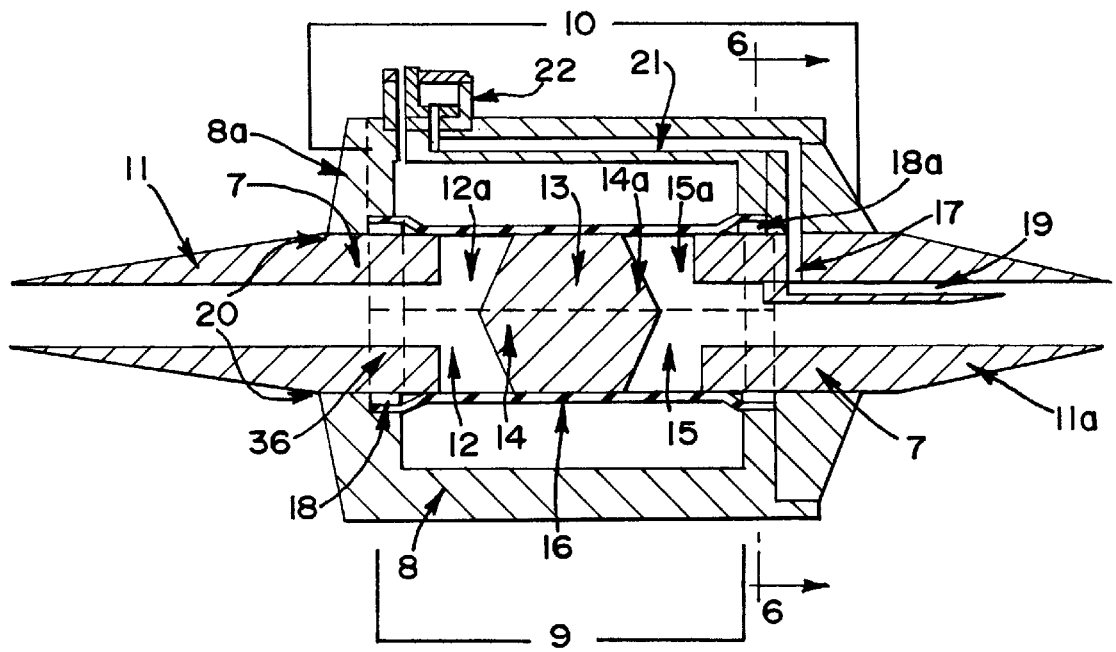
Figure 6:
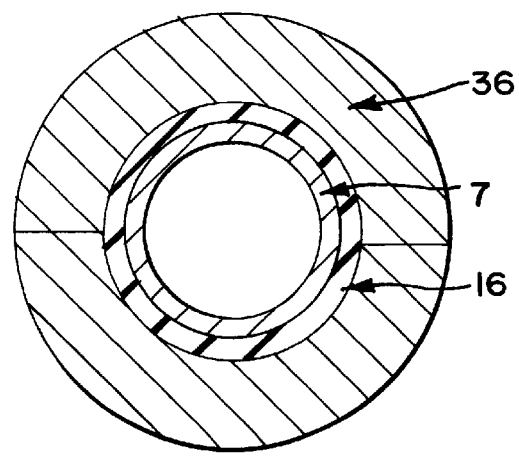

What is claimed is:

1. A vacuum dosing device comprising of:
   (a) a cylindrical tube encompassed by a cylindrical section case, said tube extending proximally and distally through said case, forming conical shaped ends, at least two first openings, said first openings located on either end of tube prior to the conical shaped ends, said first openings being diametrically opposite one another;
   said proximal conical shaped end of said tube having a vacuum source, proximal to said vacuum source and distal to said distal first openings; a semicylindrical shaped deflector extending from the proximal end of said tube to the distal end of said tube;
   (b) said tube having an outer and inner wall; a rubber cylindrical tube within the cylindrical section case;
   (c) said case having a top and bottom semicylindrical section, each semicylindrical section having an inner and outer wall, said semicylindrical sections providing a clearance between the outer wall of said tube and the inner wall of said case;
   each of said top and bottom semicylindrical sections having a left and right lid on either end thereof, said lids connecting together to form the case; said connected lids having openings on either side, said opening having an inner and outer edge, said inner edge of said semicylindrical openings forming holding straps around said rubber tube;

a second opening located adjacent to said left lid of said top semicylindrical section of said case, a third opening located above the deflector, said third opening having a diameter equal to that of the first openings in the tube;

a thin tube originating at the second opening adjacent to the left lid and running horizontal from the left lid to the right lid then vertically through the right lid to the third opening;

(d) a valve box located above said semicylindrical section of said case and adjacent the left lid, said valve box having a lever opening to said vacuum source;

said valve box having a first section located on the base, and two planes, one top central plane and another coaxial with the latter, determining a gutter surrounding the top central plane, a fourth opening in the center of said gutter connecting said valve box with the vacuum source;

a second section, comprising a cavity located in the forward part of the first section communicating with the inside of the case, through a fifth opening in the case;

(e) said gutter having a ring, with a rod perpendicular to said ring at one end thereof; a valve lid extending parallel to said ring;

said valve lid having a fourth opening, said rod extending through said opening for the free displacement of the rod in a reciprocal vertical movement;

wherein said reciprocal motion of said rod results in a vacuum in said case causing an expansion of said cylindrical tube, allowing passage of air or aspirated material between said first holes.

2. A vacuum dosing device according to claim 1, wherein said cylindrical section case is comprised of one continuous cylindrical unit.

3. A vacuum dosing device according to claim 1, wherein said cylindrical tube comprises an elastic material.

4. A vacuum dosing device according to claim 1, wherein between said openings in the middle of said cylindrical case is a partition wall, said partition wall having a free face which projects into the tube in a square base right pyramidal shaped coaxial with the tube.

5. A vacuum dosing device according to claim 1, wherein said rubber cylindrical tube having an internal diameter equal in diameter to the greater end of said conical end or said tube.

6. A vacuum dosing device according to claim 1, wherein said end of said rubber tube is mounted to the greater diameter of said conical shaped ends.

7. A vacuum dosing device according to claim 1, wherein said cylindrical valve box is comprised of two sections.

8. A vacuum dosing device according to claim 1, wherein said gutter is comprised of a rectangular section.

9. A vacuum dosing device according to claim 1, wherein said cylindrical tube is solid.

* * * * *

UNITED STATES PATENT AND TRADEMARK OFFICE
CERTIFICATE OF CORRECTION

PATENT NO. : 6,350,250 B1
DATED : February 26, 2002
INVENTOR(S) : Crosa Dorado

It is certified that error appears in the above-identified patent and that said Letters Patent is hereby corrected as shown below:

Column 1,
Line 21, begin new paragraph after "stand-by state."
Line 43, delete "troncoconical" and replace it with -- conical --.
Line 44, delete "one" and replace it with -- One --.
Line 60, begin new paragraph after "15 mm thick."
Line 67, delete "ellastic" and replace it with -- elastic --.

Column 2,
Line 6, begin new paragraph after "(16)."
Line 10, begin new paragraph after "(7)."
Line 11, delete "semicircular section" and replace it with -- semicylindrical shaped --.
Line 11, insert -- or -- between "deflector" and "gutter".
Line 15, delete "troncoconical" and replace it with -- conical --.
Line 33, delete "tree" and replace it with -- three --.
Line 50, delete "date" and replace it with -- dated --.

Column 3,
Line 1, delete "Operation" and replace it with -- OPERATION --.
Line 22, insert -- of -- between 'pressure" and "the".
Line 36, delete "Advantages" and replace it with -- ADVANTAGES --.
Line 40, begin new paragraph after "vacuum."
Line 41, begin new paragraph after "perfect."
Line 51, delete "equipments and replace it with -- equipment --.
Line 51, begin new paragraph after "hospitals."
Line 54, delete "ellastic" and replace it with -- elastic --.

Column 4,
Line 24, delete "sagittal section" and replace it with -- cross sectional --.
Line 25, delete "section" and replace it with -- sectional --.
Line 28, insert -- A -- after "FIG. 7".
Line 28, delete "Sagittal section" and replace it with -- cross sectional --.
Line 29, insert -- A -- after "FIG. 8".
Line 29, delete "Sagittal section" and replace it with -- cross sectional --.
Line 31, insert -- A -- after "FIG. 9".
Line 31, delete "Cross section" and replace it with -- cross sectional --.

UNITED STATES PATENT AND TRADEMARK OFFICE
CERTIFICATE OF CORRECTION

PATENT NO. : 6,350,250 B1
DATED : February 26, 2002
INVENTOR(S) : Crosa Dorado

It is certified that error appears in the above-identified patent and that said Letters Patent is hereby corrected as shown below:

<u>Column 4, cont'd,</u>
Line 33, insert -- A -- after "FIG. 10".
Line 33, delete "Cross section" and replace it with -- cross sectional --.
Line 39, 41 and 43, delete "section" and replace it with -- sectional --.

Signed and Sealed this

Twenty-seventh Day of May, 2003

JAMES E. ROGAN
*Director of the United States Patent and Trademark Office*